United States Patent [19]

Gerspacher et al.

[11] Patent Number: 5,359,083
[45] Date of Patent: Oct. 25, 1994

[54] PROCESS FOR THE PREPARATION OF SUBSTITUTED INDOLES

[75] Inventors: Marc Gerspacher, Aeschi; Alfred Sallmann, Bottmingen, both of Switzerland

[73] Assignee: Ciba-Geigy Corporation, Ardsley, N.Y.

[21] Appl. No.: 195,891

[22] Filed: Feb. 10, 1994

Related U.S. Application Data

[63] Continuation of Ser. No. 964,186, Oct. 21, 1992, abandoned.

[30] Foreign Application Priority Data

Oct. 25, 1991 [CH] Switzerland ............ 03136/91

[51] Int. Cl.$^5$ .................... C07D 209/04; C07C 69/96
[52] U.S. Cl. .................... 548/485; 548/490; 558/260
[58] Field of Search ................ 548/455, 490; 558/260

[56] References Cited

U.S. PATENT DOCUMENTS

| | | | |
|---|---|---|---|
| 4,837,235 | 6/1989 | Bernstein et al. | 514/234.5 |
| 4,859,692 | 8/1989 | Bernstein et al. | 514/381 |
| 4,918,094 | 4/1990 | Bernstein et al. | 514/419 |
| 5,096,917 | 3/1992 | Sallman | 514/415 |

FOREIGN PATENT DOCUMENTS

| | | | |
|---|---|---|---|
| 0199543 | 10/1986 | European Pat. Off. | 548/510 |
| 199543 | 10/1986 | European Pat. Off. | 548/510 |
| 0220066 | 4/1987 | European Pat. Off. | 548/510 |
| 0227241 | 7/1987 | European Pat. Off. | 548/510 |
| 0455596 | 11/1991 | European Pat. Off. | 548/510 |

OTHER PUBLICATIONS

Matassa, et al.; "Evolution of a Series of Peptidoleukotriene Antagonists: Synthesis and Structure/Activity Relations of 1,3,5-Substituted Indoles and Indazoles", J. Med. Chem. 1990, 33, 1781–1790.
Chemical Abstracts, vol. 100, abstract 210430$_2$, Pozdnev, V. F., SU 1,077,881, 1984.

*Primary Examiner*—Mary C. Lee
*Assistant Examiner*—Joseph K. McKane
*Attorney, Agent, or Firm*—Irving M. Fishman; Karen G. Kaiser

[57] ABSTRACT

The invention relates to a novel process for the preparation of compounds of formula I wherein R is straight-chain $C_2$–$C_4$alk-1-en-1-yl, and salts thereof, and to a novel starting material and the use thereof.

7 Claims, No Drawings

PROCESS FOR THE PREPARATION OF SUBSTITUTED INDOLES

This is a continuation of Ser. No. 07/964,186, filed Oct. 21, 1992, now abandoned.

The invention relates to a novel process for the preparation of compounds of formula I

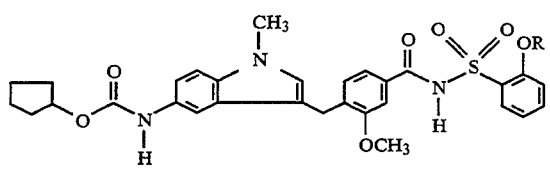

wherein R is straight-chain $C_2$–$C_4$alk-1-en-1-yl, or salts thereof, and to a novel starting material and the use thereof.

The compounds I and their pharmaceutically acceptable salts have valuable pharmacological properties, especially a pronounced antagonistic action with respect to leucotrienes.

For example, in vitro in a concentration range of from approximately 0.001 to approximately 1 μmol/l, they inhibit smooth muscle contraction induced by leucotriene $D_4$ ($LTD_4$). That action, which is referred to as $LTD_4$-antagonism, can be verified experimentally, for example, by using synthetic leucotriene $D_4$ (in the form of the potassium salt) to induce contractions in segments that have been removed from the ileum of a guinea pig weighing from 300 to 400 g and have been incubated in an organ bath in Tyrode's solution at 38° C. while gassing with a mixture of 95% oxygen and 5% carbon dioxide at a weight of 1 g, and recording those contractions isotonically. The degree to which the contractions are inhibited by the test compound is determined in the form of the $IC_{50}$ after 2 minutes' pre-incubation, the $IC_{50}$ being the concentration at which the test contractions are reduced by 50%.

The compounds I and their pharmaceutically acceptable salts also have excellent action in vivo. For example, in the standard bronchoconstriction test on guinea pigs, a pronounced $LTD_4$-antagonistic effect is observed on administering an aerosol solution comprising from approximately 0.00001 to approximately 1% by weight test compound. In that test model, male guinea pigs weighing from 400 to 700 g are anesthetized intraperitoncally with 1.4 g/kg of urethane, and a polyethylene cannula is introduced into the jugular vein. A second polyethylene cannula is introduced into the trachea. A cannula introduced into the oesophagus and connected to a Statham pressure transducer is used to record the pressure in the oesophagus. The animal is placed in a plexiglass chamber that can be closed in an air-tight manner and that is connected to a Fleisch tube No. 000 and a Validyne transducer MP 45-1. That arrangement is used to measure the flow. After the surgical preparation of the experimental animals, a certain period is allowed to elapse so that the pulmonary functions can stabilise. The test compound is then administered in accordance with the following protocol. The experimental animals are exposed for one minute to a 1% (weight/volume) aerosol solution of the test compound or to distilled water (for control purposes). A Monaghan ultrasonic spray device (Model 670), of which the particle size varies from 1 to 8 microns with a predominant portion of 3 microns, is used for all test compounds that are administered by inhalation. Aqueous solutions and DMSO/water mixtures are each freshly prepared and introduced with an on-stream drug vial into the chamber of the spray device. The spray produced is administered to the experimental animals by way of a glass chamber that has a capacity of 65 ml and is connected to the trachea by means of a cannula. When the treatment time has elapsed, $LTD_4$ (0.3 μg/ml) is administered for a period of 2 minutes using a second Monaghan ultrasonic spray device (Model 670) and by way of an identical glass chamber. The reduction in compliance is read in the third minute after $LTD_4$ administration, the average value of three animals being compared with the average value of three control animals and the percentage inhibition of compliance (% inhibition) being calculated in accordance with the following formula:

$$\% \text{ inhib.} = 100 - \frac{(100 - \text{compliance preparation}) \cdot 100}{(100 - \text{compliance control})}$$

If different concentrations of active ingredient are tested, the percentage inhibition is recorded for each concentration, "log concentration" being entered on the abscissa against "percentage inhibition" on the ordinate. The $IC_{50}$ is then determined by linear regression analysis.

The compounds I and their pharmaceutically acceptable salts also have the specific and therapeutically very important advantage of having a relatively long duration of action.

The compounds I and their pharmaceutically acceptable salts can accordingly be used therapeutically in all cases where the action of leucotrienes leads to pathological conditions, and can alleviate or eliminate those conditions. Leucotrienes play a significant part, inter alia, in the development of allergic and inflammatory processes. Accordingly, the compounds I and their pharmaceutically acceptable salts can be used, for example, as active ingredients in anti-allergic agents that are employed, for example, in the treatment of allergic conditions and disorders, such as, especially, asthma, but also hay fever and obstructive pulmonary diseases, including cystic fibrosis.

Intensive efforts have been made to develop an inexpensive process that has especially high yields and is easier to perform, and also to develop processes in which the end product can be obtained while largely avoiding unstable intermediates.

The novel process is carried out as follows:

a) a compound of formula IV

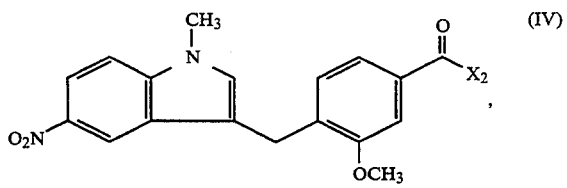

wherein $X_2$ is (IVa)
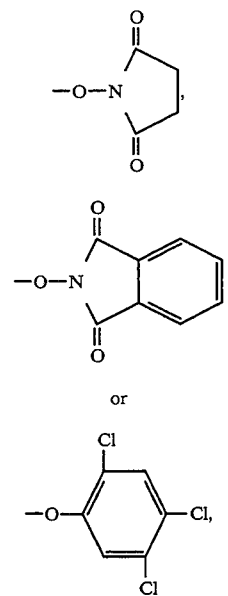
(IVb)

or (IVc)

is reduced in a one-pot process, that is to say, without isolation of intermediates, and is simultaneously N-acylated with the compound of formula V

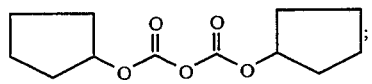
(V)

and b) a compound of formula VIa so obtainable

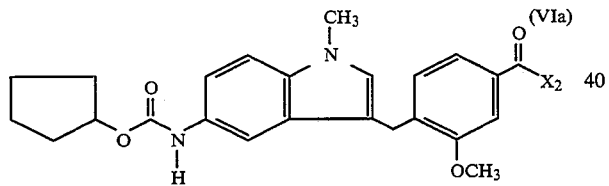
(VIa)

is reacted with a compound of formula VIb

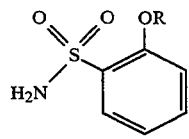
(VIb)

or with a salt thereof.

Process Step a), especially, has surprisingly proved to be especially advantageous because that reduction and N-acylation step results in unexpectedly high yields. The present invention accordingly relates also to the acylation reagent of formula V, dicyclopentyl dicarbonate, and to its preparation and use, for example as an acylation reagent for the introduction of a cyclopentyloxycarbonyl group, and to that process stage.

The preparation of the starting material of formula V, dicyclopentyl dicarbonate, is carried out by reacting a haloformic acid cyclopentyl ester, such as chloroformic acid cyclopentyl ester, in the presence of an amine, such as a trialkylamine, for example N,N-dimethyl-N-octadecylamine, using an inorganic base, such as an alkali metal hydroxide, for example sodium hydroxide. The reaction is carried out preferably in an inert solvent, that is to say, a solvent not participating in the reaction.

In addition, the compounds of formulae IV and VIa have advantageous crystallisation properties which render additional purification steps, such as chromatography, unnecessary.

The compounds of formula IV used as starting material are prepared as follows:

a1) an ester of formula II

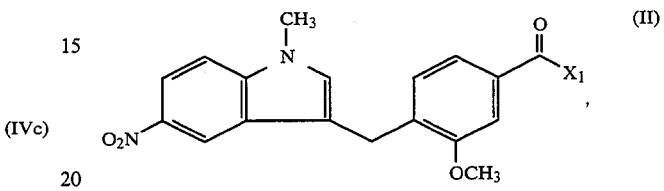
(II)

wherein $X_1$ is etherified hydroxy, is hydrolysed; and a2) in the carboxylic acid of formula III so obtainable

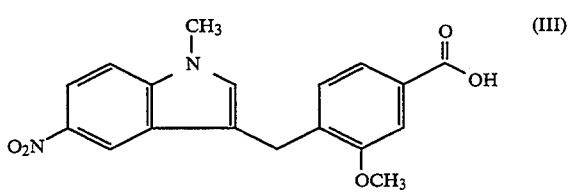
(III)

the carboxy group is activated by reaction with a compound of the formula

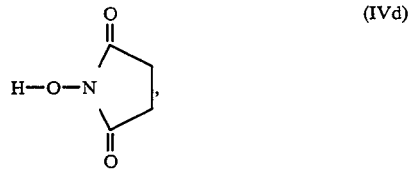
(IVd)

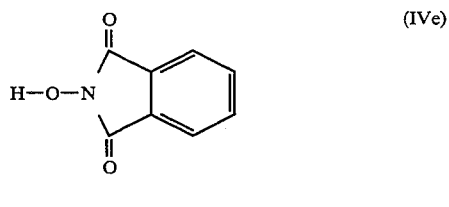
(IVe)

or

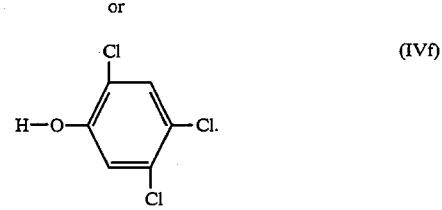
(IVf)

Surprising advantages are obtained by using that novel process sequence [Process Steps a1), a2), a) and b)]. For example, the total yield is high, and the isolation of readily decomposing amino intermediates, which requires expensive purification steps, is rendered superfluous.

The compounds of formula IV can also be obtained as follows:

1) in the compound of formula IIIa

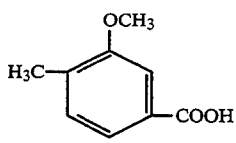

the carboxy group is activated by reaction with a compound of formula IVd, IVe or IVf (see above); and a compound of formula IIIb so obtainable

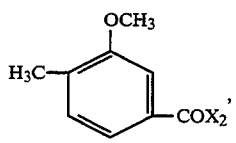

wherein $X_2$ is the radical IVa, IVb or IVc (see above), is halogenated; and 3) a compound of formula IIIc so obtainable

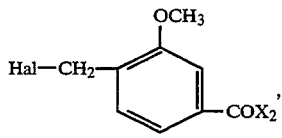

wherein Hal is halogen and $X_2$ is as defined under formula IIIb, is reacted with the compound of formula IIId

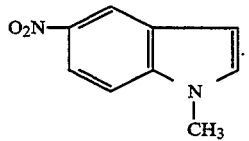

Within the scope of the invention, when the radical R contains more than two carbon atoms and may accordingly have the (E) or (Z) configuration, the compounds of formula I may be in the form of stereoisomers, for example in the form of pure diastereoisomers or mixtures of diastereoisomers. Compounds I in which the radical R has the stereochemistry, disclosed by way of example are preferred within the scope of the invention.

Salts of compounds of formula I are especially pharmaceutically acceptable salts, for example acid addition salts that are formed, for example, with strong inorganic acids, such as mineral acids, for example sulfuric acid, a phosphoric acid or a hydrohalic acid, with strong organic carboxylic acids, such as lower alkanecarboxylic acids, for example acetic acid, such as unsaturated or saturated dicarboxylic acids, for example malonic, maleic or fumaric acid, or such as hydroxycarboxylic acids, for example tartaric acid or citric acid, or with sulfonic acids, such as lower alkanesulfonic acids or unsubstituted or substituted benzenesulfonic acids, for example methane- or p-toluene-sulfonic acid, or salts with bases, such as corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-lower alkylamines, such as hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethyl- and tert-butyl-amine, suitable di-lower alkylamines are, for example, diethyl- and diisopropyl-amine and suitable tri-lower alkylamines are, for example, trimethyl- and triethyl-amine. Corresponding hydroxy-lower alkylamines are, for example, mono-, di- and tri-ethanolamine; hydroxy-lower alkyl-lower alkylamines are, for example, N,N-dimethylamino- and N,N-diethylamino-ethanol; a suitable polyhydroxy-lower alkylamine is, for example, glucosamine. Salts that are not suitable for pharmaceutical uses are also included because they can be used, for example, for the isolation or purification of free compounds I and their pharmaceutically acceptable salts.

Hereinbefore and hereinafter, unless otherwise defined, radicals and compounds termed "lower" are to be understood as being those having up to and including 7, especially up to and including 4, carbon atoms.

Straight-chain $C_2$–$C_4$alk-1-en-1-yl is vinyl, (Z)-propen-1-yl, (E)-propen-1-yl, (Z)-but-1-en-1-yl or (E)-but-1-en-1-yl.

Compounds of formula I wherein R is vinyl, (Z)-propen-1-yl or (E)-propen-1-yl and their salts are preferred within the scope of the invention.

Compounds of formula I wherein R is vinyl (Z)-propen-1-yl and their salts are especially preferred within the scope of the invention.

The compound of formula I wherein R is vinyl and its salts are very especially preferred within the scope of the invention.

The reactions described hereinbefore and hereinafter are carried out, for example, in the absence or, generally, in the presence of a suitable solvent or diluent or a mixture thereof, the reactions being effected, as required, with cooling, at room temperature or with heating, for example in a temperature range of approximately from −80° C. up to the boiling temperature of the reaction medium, preferably from approximately −20° C. to approximately +150° C., and, if necessary, in a closed vessel, under pressure, in an inert gas atmosphere and/or under anhydrous conditions. Especially advantageous reaction conditions can be found in the Examples.

The starting material mentioned hereinbefore and hereinafter, which is used for the preparation of the compounds I and their salts, is known or can be prepared in accordance with methods known per se, for example in accordance with the procedures described hereinafter.

The above statements made in connection with salts of compounds I apply analogously to salts of starting materials mentioned hereinbefore and hereinafter.

Process Step a1):

Etherified hydroxy $X_1$ is especially lower alkoxy, such as methoxy.

The hydrolysis of the ester is carried out in a manner known per se, for example in the presence of a basic agent or an acidic agent, such as a mineral acid. Suitable acids are, for example, sulfuric acid, a phosphoric acid or a hydrohalic acid, or a strong organic carboxylic acid, such as unsubstituted or substituted, for example halo-substituted, $C_1$–$C_4$alkanecarboxylic acids, for example acetic acid. Suitable bases are, for example, alkali metal hydroxides, hydrides, amides, alkanolates, carbonates, triphenylmethylides, di-lower alkylamides, aminoalkylamides or lower alkylsilylamides; also naphthaleneamines, lower alkylamines, basic heterocycles, ammonium hydroxides, and also carbocyclic amines. There may be mentioned by way of example: lithium hydroxide, hydride and amide, sodium hydroxide, hydride and amide, potassium tert-butanolate, silver or potassium carbonate, lithium triphenylmethylide, lithium diisopropylamide, potassium 3-(aminopropyl)-amide, potassium bis(trimethylsilyl)amide, dimethylaminonaphthalene, di- or triethylamine, and ethyuldiisopropyldamine, N-methylpiperidine, pyridine, benzyltrimethylammonium hydroxide, 1,5-diazabicyclo[4.3.0]non-5-ene (DBN) and 1,8-diazabicyclo[5.4.0]undec-7-ene (DBU).

The hydrolysis is preferably carried out with lithium hydroxide.

The solvents used are especially inert solvents, that is to say, solvents not participating in the reaction, or mixtures thereof, for example ethers, such as tetrahydrofuran or dioxane, alcohols, such as lower alkanols, for example methanol, ethanol or isopropanol, or water.

Process Step a2):

Preferably, the radical

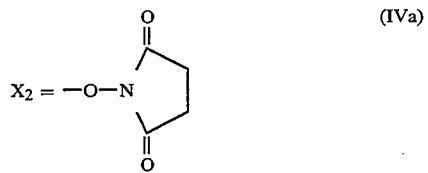

is introduced to activate the carboxy group.

The activation of the carboxy group in compounds of formula III is carried out in the presence of a condensation agent by reaction with the corresponding hydroxy compound, that is to say, a compound of formula IVd, IVe or IVf (see above).

A suitable condensation agent is, for example, a carbodiimide, such as diethyl- or dicyclohexyl-carbodiimide, or, when 2,4,5-trichlorophenol is used in the reaction, also a base, such as a di-lower alkylaminopyridine, for example dimethylaminopyridine.

The reaction is preferably carried out in an ether, such as tetrahydrofuran or dioxane, a halogenated hydrocarbon, such as chloroform or carbon tetrachloride, also an ester, such as ethyl acetate, or an amide, such as dimethylformamide.

Process Step a):

The reduction is carried out using a hydrogenation agent promoting the reduction of the nitro group in the presence of an activated carboxy group. A suitable method of reduction is especially hydrogenation with hydrogen in the presence of a hydrogenation catalyst, such as Lindlar's catalyst or palladium-on-carbon.

The N-acylation with the compound of formula V is carried out without using a base that assists N-acylation.

The solvent used is, for example, an ether, such as tetrahydrofuran, an amide, such as dimethylformamide, or an ester, such as ethyl acetate.

Process Step b):

The reaction to form the sulfonamide is carried out, for example, in the presence of a base promoting condensation. A suitable base is, for example, 1,8-diazabicyclo[5.4.0]undec-7-ene (DBU), 1,5-diazabicyclo[4.3.0]non-5-ene (DBN), an alkali metal alcoholate, such as sodium methanolate or potassium tert-butanolate, benzyltrimethylammonium hydroxide (Triton B) or a strongly basic amine, such as di-lower alkylaminopyridine, for example dimethylaminopyridine. It is preferable to use DBU as the base.

The solvent used is, for example, an ether, such as tetrahydrofuran, a suitable nitrile, such as acetonitrile, an amide, such as dimethylformamide, or a halogenated hydrocarbon, such as carbon tetrachloride.

Process Step 1 ):

The activation of the carboxylic acid is advantageously carried out in the manner described in Process Step a2).

Process Step 2):

The halogenation is carried out in a manner known per se, for example using an N-halosuccinimide, such as N-bromosuccinimide.

The solvent used is, for example, a halogenated hydrocarbon, such as carbon tetrachloride.

Process Step 3):

The alkylation of the indole derivative IIId with the benzyl halide of formula IIIc is carried out in a manner known per se, for example in the presence of silver carbonate and, for example, using toluene as the solvent.

The invention relates also to those forms of the process according to which a compound obtainable as intermediate at any stage of the process is used as starting material and the remaining steps are carried out, or a starting material is used in the form of a derivative or salt or, especially, is formed under the reaction conditions.

The following Examples illustrate the invention described above but they are not intended to limit the scope thereof in any way. Temperatures are given in degrees Celsius.

EXAMPLE 1

[Process Step b)]

9.0 ml of 1,8-diazabicyclo[5.4.0]undec-7-ene (DBU) are added at room temperature, with stirring and the introduction of argon, to a suspension of 10.0 g of 4-[5-(cyclopentyloxycarbonylamino)-1-methylindol-3-ylmethyl]-3-methoxybenzoic acid N-succinimide ester and 4.1 g of 2-vinyloxybenzenesulfonic acid amide in 150 ml of acetonitrile. The resulting solution is stirred for 1.5 hours at room temperature and then rendered acidic with 90 ml of 1N hydrochloric acid (pH 4). The acetonitrile is distilled off at 10° C. under 11 torr. The aqueous suspension is extracted twice with 250 ml of ethyl acetate each time. The organic phases are combined and washed twice with 50 ml of water each time and twice with 50 ml of brine each time, dried over magnesium sulfate and concentrated by evaporation at 40° C. under 11 torr. The residue is subjected to flash chromatography on 500 g of silica gel [eluant: hexane/ethyl acetate/acetonitrile (15/5/3)]. The 2-vinyloxybenzenesulfonic acid N-[4-(5-cyclopentyloxycarbonylamino-1-methylindol-3-ylmethyl)-3-methoxybenzoyl]amide obtained in that manner is recrystallised from methanol. Yield 61%, white crystals of m.p. 185°–188° C.

The starting material is prepared as follows:

Process Step a1):

367.0 g of 3-methoxy-4-(1-methyl-5-nitroindol-3-ylmethyl)-benzoic acid methyl ester are dissolved, with heating, in 3.7 liters of tetrahydrofuran and 700 ml of methanol. The resulting solution is cooled to room temperature and a solution of 155.0 g of lithium hydroxide monohydrate in 1.3 liters of water is added, with stirring. The resulting suspension is caused to dissolve by the addition of 1.0 liter of methanol. The resulting turbid brown solution is stirred for 15 hours at room temperature and, after the addition of activated carbon, is filtered. The orange filtrate is concentrated by evaporation in vacuo at 40° and the residue is dissolved in 2.0 liters of water. 350 ml of 37% hydrochloric acid are added to the aqueous solution and the crystals which separate out are filtered off. The residue is suspended in 1.5 liters of water and the suspension is filtered off. The residue is washed with 500 ml of methanol and dried for 15 hours at 50° under 0.01 torr. The 4-(1-methyl-5-nitroindol-3-ylmethyl)-3-methoxybenzoic acid has a melting point of 263°–265°. Yield 99%.

Process Step a2):

A suspension of 340.0 g of 4-(1-methyl-5-nitroindol-3-ylmethyl)- 3-methoxybenzoic acid in 12.0 liters of tetrahydrofuran is heated to boiling point, with stirring, in a nitrogen atmosphere. The resulting solution is cooled to room temperature and 123.0 g of N-hydroxysuccinimide and 238.0 g of N,N'-dicyclohexylcarbodiimide are added, with stirring. The resulting suspension is stirred for 15 hours at room temperature and filtered off. The residue (N,N'-dicyclohexylurea) is washed with 200 ml of tetrahydrofuran and the combined filtrates are concentrated to dryness in vacuo at 40°. The yellow crystalline residue is suspended in 2.0 liters of ethyl acetate and the suspension is left to stand for 15 hours at 5° and filtered off. The residue is washed with 200 ml of ethyl acetate. The 3-methoxy-4-(1-methyl-5-nitroindol-3-ylmethyl)-benzoic acid N-succinimide ester has a melting point of 204°–208°. Yellow crystals. Yield 95%.

Process Step a):

After the addition of 5.0 g of palladium-on-carbon catalyst (10%), a solution of 87.5 g of 3-methoxy-4-(1-methyl-5-nitroindol-3-ylmethyl)-benzoic acid N-succinimide ester and 70.0 g of dicyclopentyl dicarbonate in 1.2 liters of tetrahydrofuran is hydrogenated under normal pressure and at room temperature. After 4 hours, the absorption of hydrogen has ceased. The catalyst is separated off by filtration through a layer of Hyflo Super Cel and then the residue is washed with 200 ml of tetrahydrofuran. The filtrate is concentrated by evaporation at 40° under 11 torr. The residue, a greyish crystal mass, is suspended in 200 ml of diethyl ether. The suspension is filtered off with suction and then the residue is washed with 100 ml of diethyl ether and dried for 15 hours at 40° under 0.01 torr. The 4-[5-(cyclopentyloxycarbonylamino)-1-methylindol-3-ylmethyl]-3-methoxybenzoic acid N-succinimide ester has a melting point of 190°–193°. Yield 93%.

Preparation of the dicyclopentyl dicarbonate:

A solution of 132.0 g of sodium hydroxide in 2.0 liters of water is added dropwise over a period of 30 minutes, with rapid stirring, to a solution of 547.0 g of chloroformic acid cyclopentyl ester and 1.0 ml of N,N-dimethyloctadecylamine in 4.0 liters of dichloromethane. The mixture is then stirred for 20 minutes at 20°–25°. The aqueous phase is separated off and extracted with 700 ml of dichloromethane. The combined organic phases are washed with 1.0 liter of water, dried over calcium chloride and concentrated to dryness in vacuo at 30°. The residue, a brownish liquid, is distilled in a flash distillation apparatus (graphite wiper, turbo pump). The dicyclopentyl dicarbonate is in the form of a colourless liquid. B.p. 80°/0.01 torr. Yield 84%.

The 3-methoxy-4-(1-methyl-5-nitroindol-3-ylmethyl)-benzoic acid N-succinimide ester [Process Step a2)] can alternatively be prepared as follows:

Process Step 1):

2.9 g of N-hydroxysuccinimide and 5.6 g of dicyclohexylcarbodiimide are added under argon, with stirring, to a solution of 3.93 g of 3-methoxy-4-methylbenzoic acid in 100 ml of tetrahydrofuran. The mixture is stirred for 18 hours at room temperature. The white suspension is filtered off and then washed with 40 ml of tetrahydrofuran. The filtrate is concentrated to dryness by evaporation at 40° under 11 torr. The residue is dissolved in 30 ml of hot ethyl acetate. After the solution has cooled and 10 ml of ether have been added, the 3-methoxy-4-methylbenzoic acid N-succinimide ester crystallises out. Yield 75.2%, white crystals of m.p. 134°–135°.

The starting compound can be prepared, for example, as follows:

36.0 g of 3-methoxy-4-methylbenzoic acid methyl ester are dissolved in 300 ml of methanol. 25 ml of 30% sodium hydroxide solution are added dropwise to the solution. The mixture is stirred for 16 hours at room temperature and for 3 hours at 40° and concentrated by evaporation at 50° under 11 torr. The residue is dissolved in 500 ml of water and the solution is rendered acidic with concentrated hydrochloric acid (pH 1). The white crystals which separate out are isolated by filtration, washed with 40 ml of water and dried at 90° for 15 hours under 0.1 torr. The 3-methoxy-4-methylbenzoic acid has a melting point of 157°–158°. Yield 96%.

Process Step 2):

10.95 g of N-bromosuccinimide and 0.5 g of azoisobutyronitrile (AIBN) are added at room temperature, with stirring and under nitrogen, to a suspension of 14.05 g of 3-methoxy-4-methylbenzoic acid N-succinimide ester in 160 ml of tetrachloromethane. The mixture is heated under reflux for 24 hours, cooled to room temperature and filtered. The filtrate is concentrated by evaporation at 50° under 11 torr. The residue is crystallised from a mixture of 100 ml of ethyl acetate and 200 ml of hexane. The 4-bromomethyl-3-methoxybenzoic acid N-succinimide ester has a melting point of 124°–125°. Beige crystals. Yield 74.8%.

Process Step 3):

2.85 g of N-methyl-5-nitroindole and 7.5 g of silver carbonate are suspended, with stirring, in an argon atmosphere in 100 ml of toluene. The suspension is heated under reflux for 18 hours and cooled to 55°, and a solution of 5.4 g of 4-bromomethyl-3-methoxybenzoic acid N-succinimide ester is added dropwise, with stirring. The mixture is stirred for five days at 55°–60°, cooled to room temperature and filtered. The residue is then washed with 30 ml of toluene. The filtrate is concentrated by evaporation at 50° under 11 torr. The residue is chromatographed on 1000 g of silica gel using a MPLC column (eluant: ethyl acetate/hexane 3:2). The 3-methoxy-4-(1-methyl-5-nitroindol-3-yl-methyl)-benzoic acid N-succinimide ester obtained in that manner is recrystallised from ethyl acetate. Yield 37%, yellow crystals of m.p. 215°–216°.

EXAMPLE 2:

[Process Step b)]

Analogously to Example 1, 2-vinyloxybenzenesulfonic acid N-[4-(5-cyclopentyloxycarbonylamino-1-methylindol-3-ylmethyl)-3-methoxybenzoyl]-amide is obtained starting from 4-[5-(cyclopentyloxycarbonylamino)-1-methylindol-3-yl-methyl]-3-methoxybenzoic acid 2,4,5-trichlorophenyl ester and 2-vinyloxybenzenesulfonic acid amide in a yield of 62%.

The starting material is prepared as follows:
Process Step a2):

1.66 g of dicyclohexylcarbodiimide are added at room temperature, with stirring and in a nitrogen atmosphere, to a mixture of 2.38 g of 4-(1-methyl-5-nitroindol-3-ylmethyl)-3-methoxybenzoic acid [Example 1, Process Step a1)], 1.48 g of 2,4,5-trichlorophenol and 1.0 g of 4-dimethylaminopyridine in 140 ml of tetrahydrofuran. The reaction mixture is stirred at room temperature for 15 hours and filtered. The filtrate is concentrated by evaporation in vacuo at 50° and the residue is dissolved in 400 ml of chloroform, with heating. The organic phase is washed at room temperature with 50 ml of 2N hydrochloric acid and 50 ml of water and dried over magnesium sulfate, and the solution is concentrated to dryness at 40° under 11 torr. The residue is chromatographed on 350 g of silica gel (eluant: dichloromethane). The 3-methoxy-4-(1-methyl-5-nitroindol-3-ylmethyl)-benzoic acid 2,4,5-trichlorophenyl ester obtained in that manner is suspended in 50 ml of ether and isolated by filtration. Yield 67%. Yellow crystals of m.p. 235°–236°.

Process Step a):

After the addition of 0.4 g of palladium-on-carbon catalyst (10%), a suspension of 1.04 g of 3-methoxy-4-(1-methyl-5-nitroindol-3-ylmethyl)-benzoic acid 2,4,5-trichlorophenyl ester, 0.6 g of dicyclopentyl dicarbonate and 1.0 g of 1,2-dichlorobenzene in 60 ml of tetrahydrofuran is hydrogenated for 25 hours at room temperature. A further 0.8 g of catalyst and 0.5 g of 1,2-dichlorobenzene are added and the batch is hydrogenated for a further 45 hours. In order to remove the catalyst, the mixture is filtered and then the residue is washed with 50 ml of tetrahydrofuran. The filtrate is concentrated to dryness by evaporation in vacuo and the residue is triturated with 100 ml of petroleum ether, isolated by filtration and chromatographed on 190 g of silica gel using a MPLC column (eluant: dichloromethane). The resulting 4-[5-(cyclopentyloxycarbonylamino)-1-methylindol-3-ylmethyl]-3-methoxybenzoic acid 2,4,5-trichlorophenyl ester is recrystallised from ether/petroleum ether. Yield 35%. Colourless crystals of m.p. 134°–136°.

What is claimed is:

1. Dicyclopentyl dicarbonate.
2. A method for the introduction of a cyclopentyloxycarbonyl group comprising acylating a nitrate which has been reduced with dicyclopentyl dicarbonate according to claim 1.
3. A method for the introduction of a cyclopentyloxycarbonyl group comprising acylating an amine with dicyclopentyl dicarbonate according to claim 1.
4. The method of claim 2 wherein the nitrate which has been reduced is a nitro-indole wherein the nitro group is attached at the 4-, 5-, 6- or 7-position of the indole ring.

5. The method of claim 3 wherein the amine is an aminoindole wherein the amino group is attached at the 4-, 5-, 6- or 7-position of the indole ring.
6. The method of claim 2 wherein the nitrate which has been reduced is a compound of the formula

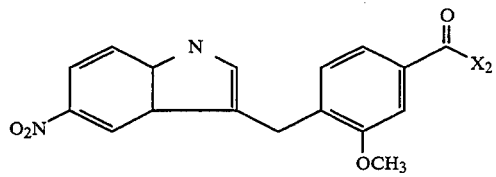

wherein $X_2$ is

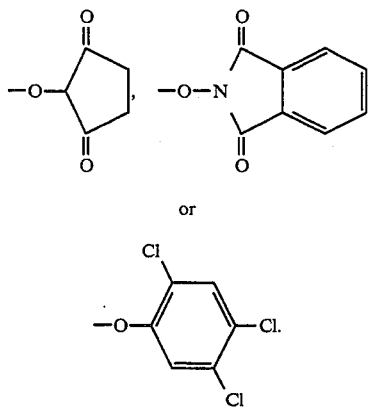

7. The method of claim 2 wherein the nitrate which has been reduced is a compound of the formula

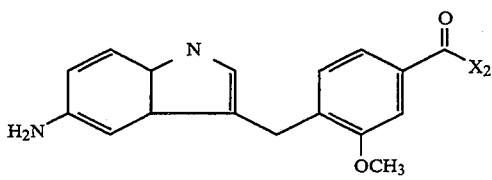

wherein $X_2$ is

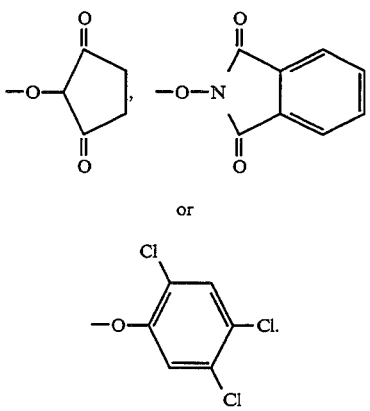

* * * * *